United States Patent [19]
Bulow et al.

[11] Patent Number: 5,665,073
[45] Date of Patent: Sep. 9, 1997

[54] PROTECTIVE SHEATH AND SECUREMENT APPARATUS AND METHOD FOR SURGICAL CONDUITS

[76] Inventors: Christi Bulow, 562 E. 1700 South, Salt Lake City, Utah 84105; Sharon Keller, 221 E. 100 South, Santaquin, Utah 84655

[21] Appl. No.: 384,777
[22] Filed: Feb. 7, 1995
[51] Int. Cl.$^6$ ............................................. A61M 5/00
[52] U.S. Cl. ................................................. 604/263
[58] Field of Search ............................. 128/856, 898; 602/3, 60, 62, 61, 63, 68, 69, 71, 72, 73; 604/192, 197, 198, 199, 263, 268, 28, 49

[56] References Cited

U.S. PATENT DOCUMENTS

| | | | |
|---|---|---|---|
| 2,522,842 | 9/1950 | Scholl | 602/63 X |
| 2,636,492 | 4/1953 | Wright | 602/61 OR |
| 3,138,156 | 6/1964 | Crowell et al. | 602/61 OR |
| 3,902,500 | 9/1975 | Dryden | 128/351 |
| 4,119,093 | 10/1978 | Goodman | 128/856 OR |
| 4,168,699 | 9/1979 | Hauser | 128/768 |
| 4,559,042 | 12/1985 | Votel | 604/263 |
| 4,725,267 | 2/1988 | Vaillancourt | 604/263 |
| 4,911,151 | 3/1990 | Rankin et al. | 602/3 OR |
| 4,943,284 | 7/1990 | Erlich | 604/263 |
| 5,358,495 | 10/1994 | Lynn | 604/263 |
| 5,362,306 | 11/1994 | McCarrer et al. | 602/60 |
| 5,404,870 | 4/1995 | Brinkerhoff et al. | 604/264 |

*Primary Examiner*—Corrine M. McDermott
*Assistant Examiner*—N. Kent Gring
*Attorney, Agent, or Firm*—J. Winslow Young

[57] ABSTRACT

A protective sheath apparatus and method for protecting surgical conduits from contamination by liquids resulting from a surgical procedure. The protective sheath also provides a restraint system for securing the various surgical conduits on the surgical field. The protective sheath is configured as a tubular element fabricated from a liquid-resistant, fabric-like material. An annular shield is affixed to one end of the tubular element and serves as the entry for inserting the surgical conduits through the tubular element. A pair of guide members are mounted to the shield and serve as a basal element over which the tubular element is longitudinally folded and as a guide for assisting in the passage of the surgical conduits through the folded tubular element. Retainer strings releasably hold the tubular element in its telescopically folded configuration. A drawstring is provided to cinch the end of the tubular element to the surgical conduits while the shield is used as a handle to extend the tubular element along the surgical conduits.

10 Claims, 5 Drawing Sheets

PROTECTIVE SHEATH AND SECUREMENT APPARATUS AND METHOD FOR SURGICAL CONDUITS

BACKGROUND

1. Field of the Invention

This invention relates to protective sleeves and, more particularly, to a novel protective sheath apparatus and method for protecting surgical conduits from gross contamination during a surgical procedure, the protective sheath also providing a securement mechanism for securing the surgical conduits to the sterile field during the surgical procedure.

2. The Prior Art

The emerging field of arthroscopy and laparoscopy as accepted surgical procedures has enjoyed an explosive growth within the past few years. This explosive growth has been made possible in large part by the advances in both the optical systems used for enabling the surgeon to visually observe the particular surgical site along with vastly improved tools for accomplishing the particular surgical procedure. These optical systems include optical fiber bundles which serve the dual purposes of introducing light into the surgical site to enable the surgeon to both observe and video record what is being seen. The surgical instruments include power driven cutters, suction lines, saline lines, fiber optic bundles for lasers, and the like.

The primary advantage afforded by these surgical procedures is that the wound site is quite small thereby requiring less anesthetic and a shorter hospital stay with a consequent more rapid recovery by the patient. Indeed, many procedures which once required extensive hospitalization are now performed routinely on an outpatient basis using these recent innovations. However, as the instrumentation becomes smaller it has also created other problems particularly for the medical professionals who provide support services to the surgeon both during and after the surgical procedure.

For example, one particularly vexing problem is that of maintaining the sterility of the various conduits used during the surgical procedure. In particular, three, four, or more conduits will enter the sterile field from the various pieces of support equipment placed around the periphery of the surgical suite. These conduits tend to slip off the operating table and become nonsterile which is an absolutely unacceptable consequence.

Perhaps an even greater problem is that of gross contamination of the conduits during the surgical procedure. This contamination is caused by the accumulation of body fluids, tissue, fats, etc. from the patient and must be removed before the particular conduit can be subjected to cold sterilization prior to reuse. Experience has shown that these items of equipment are subjected to harsh treatment through vigorous scrubbing by the medical professionals responsible for their cleanup after a surgical procedure. One result of such harsh physical treatment is the destruction of optical fibers in a fiber optical bundle along with destruction of the protective covering of a conduit, to name a few. One hospital in particular has found it necessary to have several extra sets of surgical conduits on hand at all times in order to have sufficient support capability to compensate for the times when various pieces of this equipment are returned to the manufacturer for refurbishing. Not only is this an added expense but one must also take into account the extra time required for a medical professional to scrub the various conduits. This extra handling is an added cost in that the time expended by the medical professional is costly. Also, any residual contamination results in a reduction in the effective life of the cold sterilization solution which is an added expense.

Various types of protective devices are known and included, for example, a protective device for a hypodermic needle as taught by Rosenberg (U.S. Pat. No. 4,857,060. This protective device has an annular, radially projecting membrane that is mounted to the hub of the hypodermic needle in a shirt-like fashion so that the membrane can be splayed radially to shield the operator from body fluids while performing an injection with the hypodermic needle. The hem portion of the shirt-like membrane includes a drawstring to close the membrane about the needle after withdrawal of the needle from the patient. Closure of the shirt-like membrane creates a box-like enclosure about the hypodermic needle.

Another protective device is that of Anapliotis (U.S. Pat. No. 5,239,981). Anapliotis teaches a film covering to protect a surgical instrument such as an endoscope. A circular membrane 5 has an aperture 7 therein through which the distal end of a surgical instrument is inserted into the tubular film covering 1. The film covering 1 is folded in a telescopic manner prior to extension over the surgical instrument. The circular membrane 5 is fabricated from an elastic material to accommodate the aperture 7 being stretched over various sizes, connectors, and the like, of the surgical instrument.

Hampson (U.S. Pat. No. 4,327,735) discloses a catheter assembly having a transparent, collapsible sleeve, the collapsible sleeve being sealed at one end to a hollow tube and terminating at its other end in an O-ring.

Muto (U.S. Pat. No. 4,392,853) discloses a tubular sheath of transparent, relatively limp, impervious plastic for protecting and affixing an indwelling catheter.

Cassou (U.S. Pat. No. 4,453,936) discloses a protective sleeve for a gynecological gun used in the artificial insemination of animals.

Dastgeer (U.S. Pat. No. 4,596,554) discloses a colo-rectal evacuator used for mechanically removing waste material through a patient's rectum. The evacuator is enclosed in a disposable bag into which the wastes are collected for subsequent disposal.

Palmer (U.S. Pat. No. 4,836,199) discloses an aspirating catheter tube internally disposed within and coextensive with a surrounding flexible and collapsible, sterility-preserving film envelope.

Seitz, Jr. (U.S. Pat. No. 4,877,033) discloses a sterile plastic sheath for covering a transvaginal ultrasound probe during nonoperative diagnostic examinations. A second, durable plastic sheath is fitted over the transvaginal ultrasound probe to protect it from accidental damage during storage.

Anapliotis (U.S. Pat. No. 5,061,246) discloses a tube-like covering for protecting an elongated surgical instrument. The covering is initially in a telescopically folded configuration prior to receipt therein of the surgical instrument.

Adair (U.S. Pat. No. Re. 33,854) discloses a rigid heat sterilizable outer sheath for a video endoscope. The video endoscope releasably locks into the outer sheath. The outer sheath also includes an accordion-shaped sleeve at the proximate end which can be drawn around the trailing cables of the video endoscope so that the entire endoscope is sterile for use within the operating room.

Woodgrift et al. (U.S. Pat. No. 5,149,326) discloses an adjustable catheter contamination shield having a distal fitting, a proximal fitting, and a collapsible shield disposed between the distal fitting and the proximal fitting.

Kurtzer (U.S. Pat. No. 5,168,863) discloses a covering for an endoscopic device, the covering including a pair of generally orthoganally arranged component bags to enclose the respective elements of the endoscopic device.

Erlich (U.S. Pat. No. 5,181,913) discloses a tubular sheath for a catheter for use in removing body fluids. The tubular sheath is disposed in a rolled-up fashion around the catheter to aid in the sterile disposal of the catheter.

Burton (U.S. Pat. No. 5,228,851) discloses a single-use, disposable prophylactic elastic sleeve for placement on a handle of a dental or medical instrument. Finger engaging, ring-shaped retention members on each end of the sleeve aid in placing and expanding the elastic sleeve from a collapsed position into placement over the instrument.

In view of the foregoing, it would be an advancement in the art to provide a protective sheath for encasing a plurality of surgical conduits. Another advancement in the art would be to provide a protective sheath that will not only help prevent the surgical conduits from falling off the operating table but also shield them from a substantial portion of the contamination that would otherwise be found thereon. An even further advancement in the art would be to provide a disposable sheath that can be provided in a sterile condition and easily mounted upon and removed from the surgical conduits. Such a novel apparatus and method is disclosed and claimed herein.

BRIEF SUMMARY AND OBJECTS OF THE INVENTION

This invention includes a tubular element fabricated from a fabric-like material. The material is selected from any suitable, liquid resistant material and is designed to shield the surgical conduits enclosed therein from contamination by liquids during the surgical procedure. An annular shield is mounted to one end of the tubular element to provide the entry point for passage of the surgical conduits through the tubular element. The annular shield also serves as a handle for extending the tubular element down the length of the surgical conduits while at the same time providing a barrier for the hand of the medical professional as the tubular element is extended. A pair of guide members are mounted at the opening of the annular shield and serve as a basal element over which the tubular element is longitudinally folded prior to use and as guides for the insertion of the surgical conduits through the folded tubular element. A set of strings are included for releasably holding the tubular element in its folded state. A drawstring at the end of the tubular element opposite the annular shield is used to cinch that end of the tubular element to the surgical conduits prior to extension of the tubular element.

It is, therefore, a primary object of this invention to provide improvements in protective sheaths for surgical conduits.

Another object of this invention is to provide improvements in the method of protecting surgical conduits from contamination by liquids during surgical procedures involving the surgical conduits.

Another object of this invention is to provide a sheath for one or more surgical conduits, the sheath being fabricated as a tubular element produced with a liquid resistant, fabric-like material.

Another object of this invention is to provide an annular shield for the tubular element of the protective sheath, the shield serving as the entry point for surgical conduits inserted through the tubular element.

Another object of this invention is to provide a set of ties for releasably holding the tubular element in its folded position.

Another object of this invention is to provide a drawstring on the end of the tubular element opposite the shield to adapt that end of the tubular element to being releasably cinched about the surgical conduits.

Another object of this invention is to provide a guide for the protective sheath, the guide serving as a basal element over which the tubular element may be folded as well as a guide for inserting the surgical conduits through the folded tubular element.

Another object of this invention is to provide a set of ties for releasably holding the tubular element in its folded position.

Another object of this invention is to provide a drawstring on the end of the tubular element opposite the shield to adapt that end of the tubular element to being releasably cinched about the surgical conduits.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
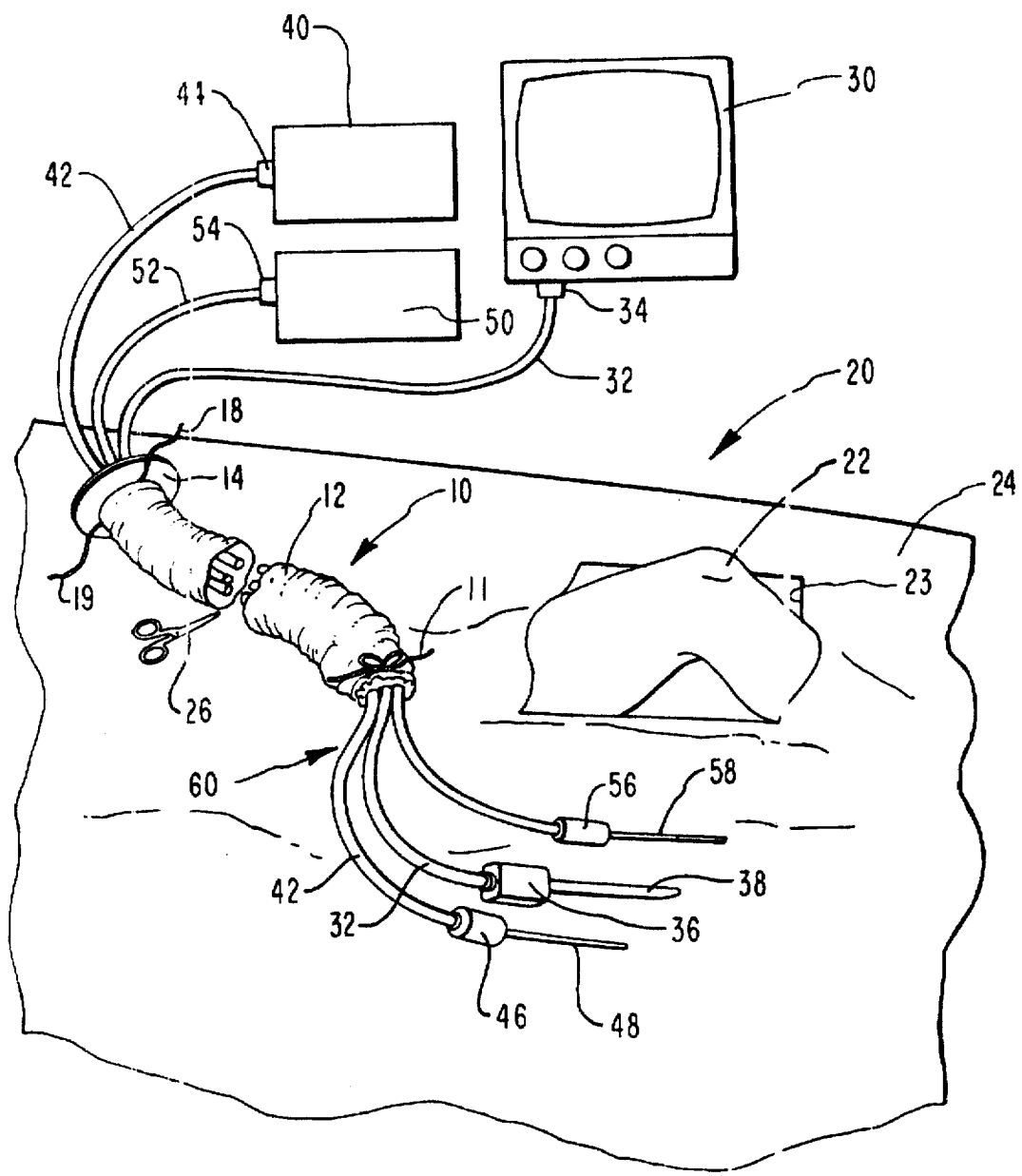
FIG. 1 is a perspective view of the novel protective sheath of this invention shown in the environment of a surgical operation.

The invention is best understood by reference to the drawing wherein like parts are designated by like numerals throughout in conjunction with the following description.

General Discussion

The novel sheath of this invention is configured as a tubular element and is fabricated from a suitable fabric-like material. One such fabric-like material is a spun blown synthetic fiber fabric referred to in the trade by its trademark, TYVEK, which is the trademark of the DuPont Corporation, Wilmington, Del. Clearly, of course, any suitable fabric-like material can be used in the practice of this invention as long as it serves as a liquid resistant barrier for protecting the surgical conduits enclosed thereby from becoming contaminated with blood or other liquids during the surgical procedure. Not only is the fabric-like material liquid resistant, it also has sufficient strength to resist tearing under normal usage. This is important since a secondary function of the protective sheath is to hold the surgical conduits together while providing an engagement mechanism to enable the medical personnel to secure the protective sheath and, therefore the surgical conduits encased therein, to the surgical drapes that define the surgical field.

An annular shield is mounted to one end of the tubular element and serves as a barrier behind which the medical professional is able to extend the end of the tubular element down the length of the surgical conduits. The shield also provides the entry point for the insertion of the proximal ends of the surgical conduits through the lumen of the tubular element. Initially, the tubular element is folded longitudinally against the shield in order to foreshorten it and thereby facilitate the passage of the surgical conduits through the tubular element. After the surgical conduits have been inserted through the folded tubular element it is unfolded by pushing the shield down the length of the surgical conduits. Removal of the tubular sheath is accomplished by pulling the distal end of the surgical conduits through the shield and then through the tubular element.

A pair of guides having what is generally referred to as a "duckbill" configuration are used to mount the tubular element to the shield and also serve as a basal element over which the tubular element is folded longitudinally. The guides also help direct the proximal ends of the surgical conduits through the folded tubular element. A pair of string ties releasably hold the tubular element in its telescopically folded configuration with respect to the guides and against the shield. A drawstring on the other end of the tubular element allows it to be cinched about the surgical conduits prior to the tubular element being extended along the length of the surgical conduits.

Detailed Description

Figure 2:
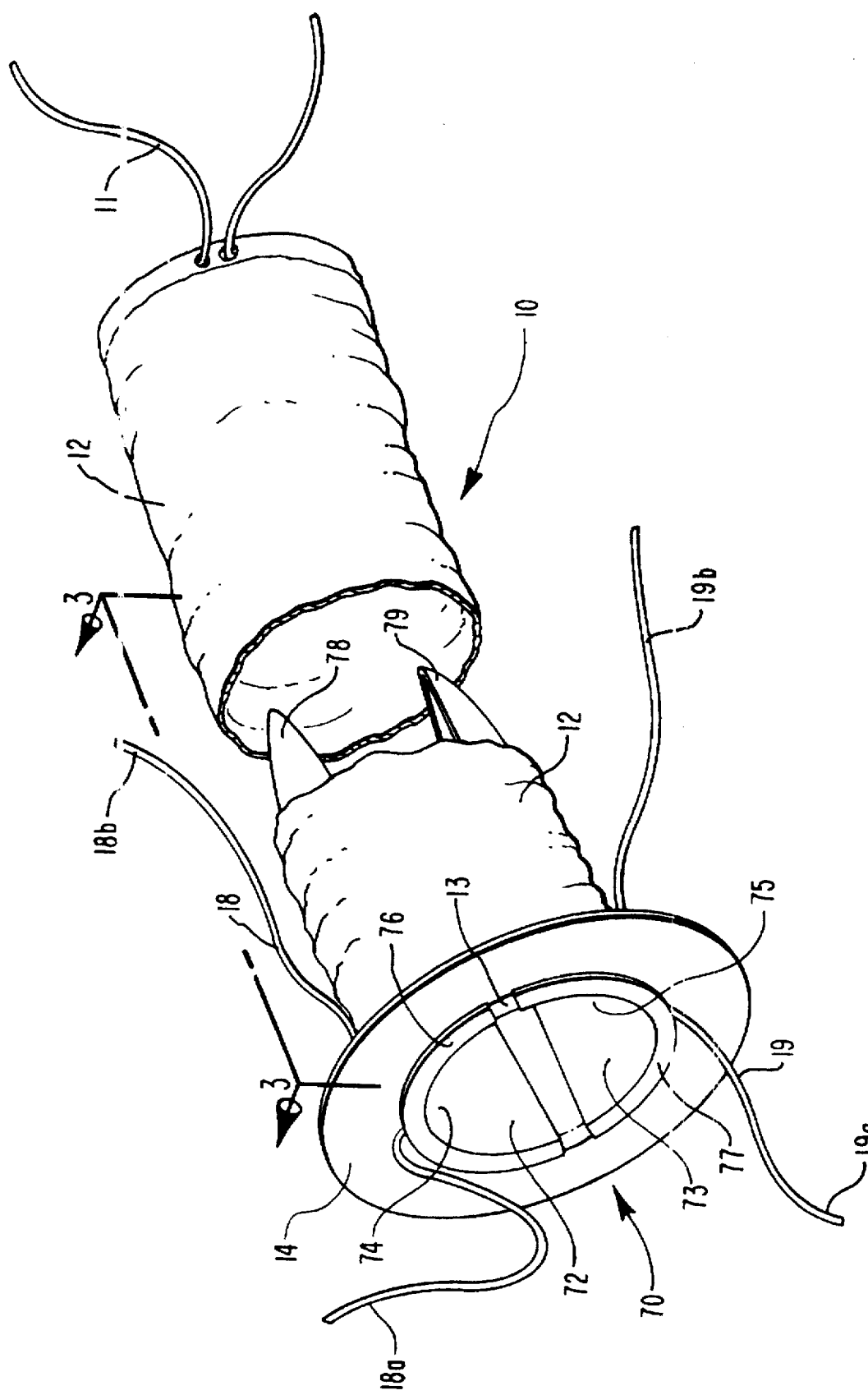
FIG. 2 is an enlarged, perspective view of the protective sheath of FIG. 1 shown foreshortened for ease of illustration.
Figure 3:
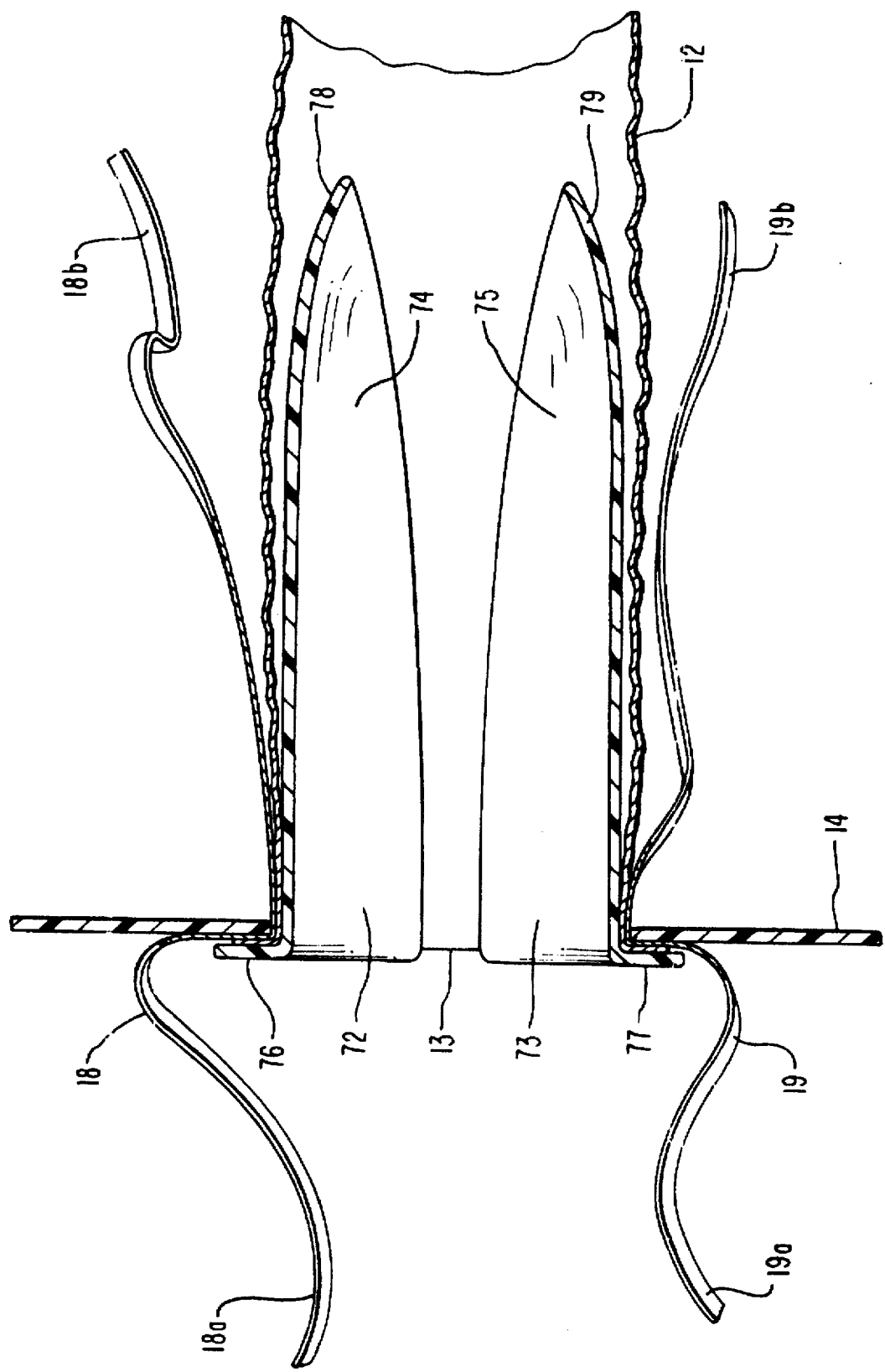
FIG. 3 is a partial, cross-sectional view of the shield end of the protective sheath taken along lines 3—3 of FIG. 2.
Figure 4:
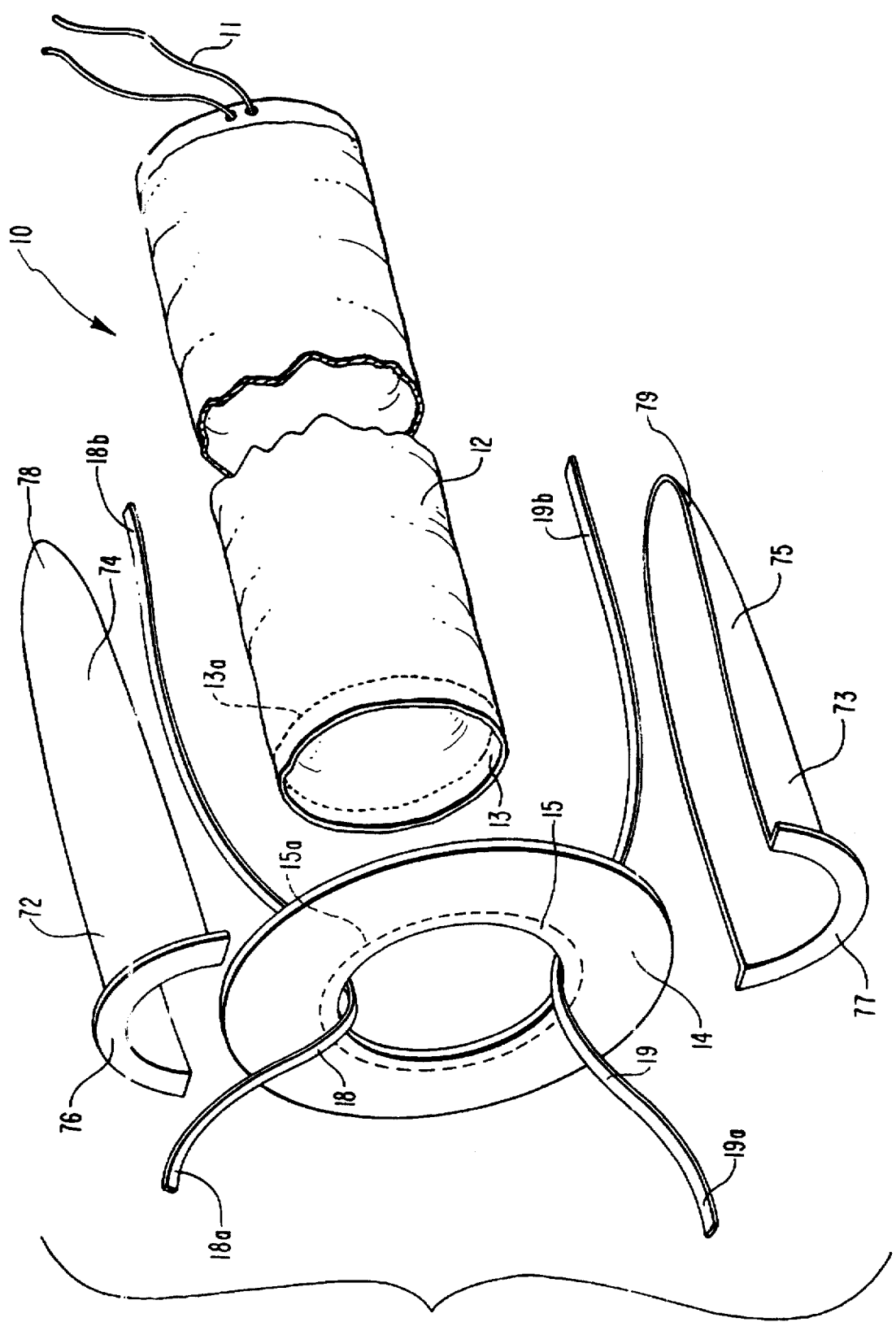
FIG. 4 is an exploded, perspective view of the protective sheath shown foreshortened for ease of illustration.

Referring now to FIG. 1, the novel protective sheath of this invention is shown generally at 10 and includes a tubular element configured as a fabric sleeve 12 having a shield 14 mounted to the distal end. Fabric sleeve 12 is prepared from any suitable, liquid resistant fabric such as TYVEK® or the like. The fabric of fabric sleeve 12 is telescopically foldable and is resistant to tearing as will be described more fully hereinafter. Shield 14 is a planar element having either a circular or oval profile with a circular (FIGS. 4 and 5) or oval (FIG. 2) hole therethrough and is prepared from a suitable material such as a card stock or plastic. A drawstring 11 is affixed to the proximal end of fabric sleeve 12 while a pair of retainer strings 18 and 19 are attached to the distal end adjacent shield 14. The function of retainer strings 18 and 19 along with drawstring 11 will be discussed more fully hereinafter.

Protective sheath 10 is shown in the environment of a surgical field shown generally at 20 and includes the knee 22 of a patient undergoing the surgical procedure, which, in this illustrative example, happens to be an arthroscopic procedure. Surgical field 20 is defined by a surgical drape 24, only a portion of which is illustrated schematically herein for sake of simplicity. Knee 22 protrudes through a hole 23 cut in surgical drape 24.

Representative examples of the various types of support equipment for this surgical procedure are shown schematically as a television monitor 30, a power supply 40, and a water supply 50. Clearly, of course, other equipment may be readily used although the described equipment is shown herein for illustrative purposes only. Each of these items of equipment includes a surgical conduit which passes across surgical field 20 to a position adjacent knee 22. For example, a monitor conduit 32 is coupled at a distal end to television monitor 30 by a connector 34. A control unit 36 and a camera probe 38 are mounted to the proximal end of monitor conduit 32. Control unit 36 enables the surgeon (not shown) to selectively adjust certain operational features of the television camera system represented by control unit 36 and camera probe 38. A power conduit 42 is coupled to power supply 40 by a connector 44. A handpiece 46 and a probe 48 are mounted to the proximal end of power conduit 42. Similarly, water supply 50 includes a water conduit 52 having a connector 54 at the distal end and a hand piece 56 and a lance 58 at the proximal end. Collectively, monitor conduit 32, power conduit 42, and water conduit 52 are referred to hereinafter as collective conduits shown generally at 60. The precise functioning of the various components associated with television monitor 30, power supply 40, and water supply 50 will not be discussed herein since these items are presented solely for the purpose of illustrating the novel features of protective sheath 10.

Protective sheath 10 is designed to enclose at least a portion of the length of monitor conduit 32, power conduit 42, and water conduit 52 (collective conduits 60). Further, protective sheath 10 acts as a restraining device to keep each of the conduits of collective conduits 60 as a compact bundle on surgical field 20. Additionally, since fabric sleeve 12 of protective sheath 10 is fabricated from a fabric-like material it can be releasably clipped to drape 24 by a suitable clip such as a hemostat 26 shown herein. In this manner, the medical professional (not shown) responsible for assuring the sterility of all items within the zone of sterile field 20 is able to use fabric sleeve 12 to securely hold the various conduits of collective conduits 60 as a distinct bundle which can then be releasably secured to surgical drape 24 at one or more locations along the length of protective sleeve 10 using an appropriate number of clips such as hemostat 26.

The proximal end of fabric sleeve 12 is cinched about the collective conduits 60 passing therethrough by drawstring 11 being pulled tightly thereabout and then tied. This feature greatly reduces the tendency for fabric sleeve 12 to creep toward the distal end of collective conduits 60 during the surgical procedure. Drawstring 11 also inhibits the migration of liquids underneath the protective covering provided by fabric sleeve 12.

Figure 5:
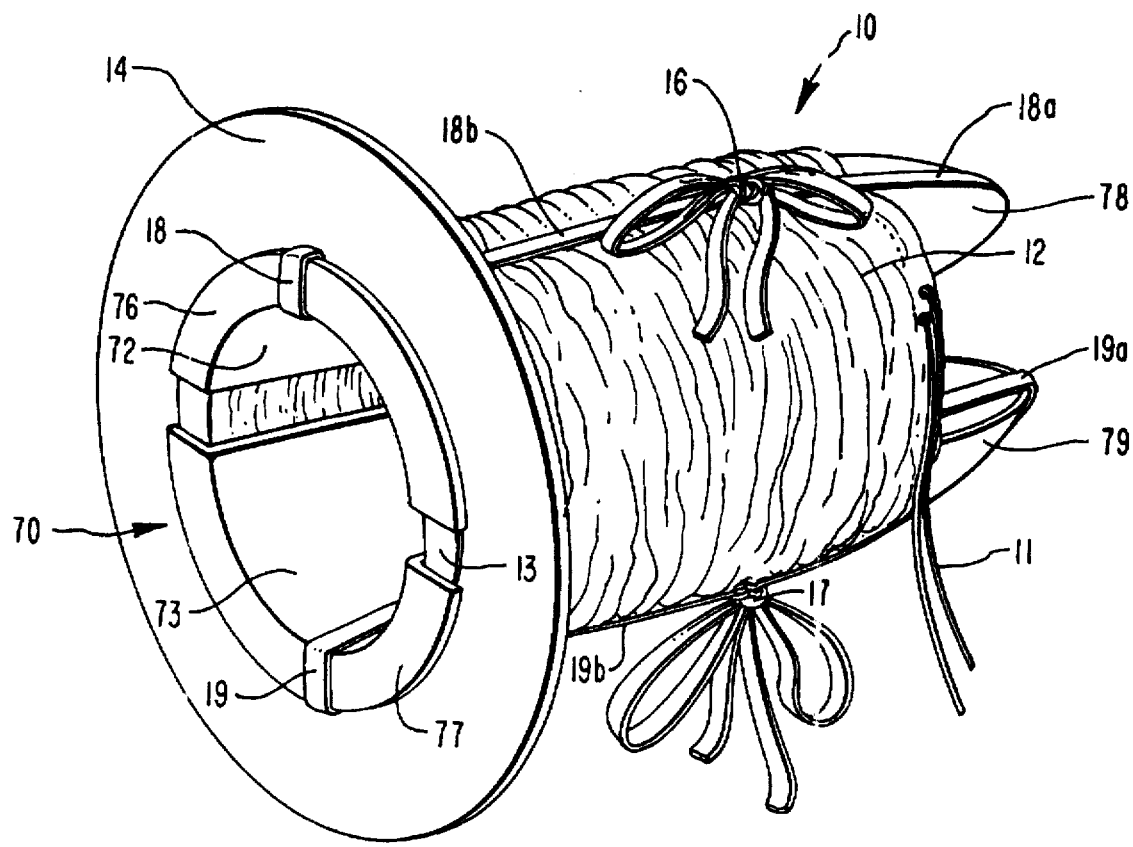
FIG. 5 is a perspective view of the protective sheath shown telescopically folded over the guide elements and against the shield.

Referring now to FIGS. 2–5, the various features of protective sheath 10 are set forth more fully particularly with respect to the relationship between fabric sleeve 12 and shield 14. Specifically, protective sheath 10 includes a sheath guide shown generally at 70. Sheath guide 70 includes a pair of opposed guide members 72 and 73. Guide members 72 and 73 are mirror images and are juxtaposed in a face-to-face relationship to form sheath guide 70. Guide member 72 is configured with a semicylindrical surface 74 terminating at the proximal end in a semicircular flange 76 and a curvilinear tip 78 at the distal end. Correspondingly, guide member 73 is configured with a semicylindrical surface 75 terminating at the proximal end semicircular flange 77 and a curvilinear tip 79 at the distal end. When combined into sheath guide 70, guide members 72 and 73 cooperate in a "duckbill" fashion to provide several useful functions, primary of which is to serve as a basal element over which fabric sleeve 12 can be longitudinally or telescopically folded as shown in FIG. 5. In this folded configuration, sheath guide 70 provides a simple mechanism for individually inserting each of the conduits that constitute collective conduits 60 through the interior of fabric sleeve 12 thereby avoiding snagging or tearing of fabric sleeve 12 by any of the components that constitute collective conduits 60. This feature is possible since sheath guide 70 or, more specifically, each of guide members 72 and 73 are fabricated from a relatively thin plastic material so as to inherently have sufficient flexibility to accommodate the outward flexure of curvilinear tips 78 and 79 as each of the respective conduits of collective conduits 60 is passed therethrough.

Semicircular flanges 76 and 77 collectively provide a bonding surface for bonding the distal end 13 of fabric sleeve 12 to shield 14. In particular and with specific reference to FIG. 4, the distal end 13 of fabric sleeve 12 that is to be bonded to shield 14 is shown by a broken line at 13a while the bonding surface 15 on shield 14 to which distal end 13 is to be bonded is delineated by a broken line 15a. Semicircular flanges 76 and 77 in effect sandwich distal end 13 against bonding surface 15 so as to present to the user of protective sheath 10 a smooth profile through which collective conduits 60 can be passed. Semicircular flanges 76 and 77 also secure retainer strings 18 and 19 to sheath 14. Retainer strings 18 and 19 are configured to releasably hold fabric sleeve in its longitudinally folded configuration shown in FIG. 5. In particular, retainer string 18 is configured with a distal end 18a and a proximal end 18b while retainer string 19 is configured with a distal end 19a and a proximal end 19b. When used as a retainer for the longitudinally folded configuration of fabric sleeve 12 as shown in FIG. 5, distal ends 18a and 19a are passed interiorly through fabric sleeve 12 and joined to the corresponding proximal end, proximal ends 18b and 19b in a knot, knots 16 and 17, respectively (FIG. 5).

The Method

Referring now to all of FIGS. 1–5, protective sheath 10 is provided in the longitudinally folded cofiguration shown in FIG. 5 which configuration is specifically designed to facilitate its use as a protective covering for collective conduits 60.

Specifically, each of the conduits of collective conduits 60 is inserted through shield 14 and then through the telescopically folded fabric sleeve 12 which is held in its telescopically folded configuration on sheath guide 70 by retainer strings 18 and 19. With protective sheath 10 engaged about collective conduits 60, knots 16 and 17 are untied to allow the medical professional (not shown) to tie drawstring 11 at a preselected location on collective conduits 60. Drawstring 11 is tied sufficiently tight about collective conduits 60 to both secure them against migration relative to protective sheath 10 and to resist entry of liquids inside fabric sleeve 12.

With drawstring 11 firmly cinched about collective conduits 60 the medical professional extends protective sheath 10 along a portion of the length of collective conduits 60 by pushing against shield 14. In particular, the medical professional places a hand against the facing surface of shield 14 and merely pushes against shield 14 to telescopically unfold fabric sleeve 12 until fabric sleeve 12 has been longitudinally unfolded its full length or a sufficient length of collective conduits 60 has been enclosed within protective sheath 10.

Protective sheath 10 can then be releasably clipped to surgical drape 24 by using one or more hemostats 26. This provides the medical professional with the capability of orienting collective conduits 60 at any preselected orientation relative to surgical field 20. Further, protective sheath 10 prevents any one of the individual conduits that constitute collective conduits 60 from slipping either away from the vicinity of knee 22 or off surgical field 20. Additionally and also importantly, protective sheath 10 protects collective conduits 60 from liquids so as to facilitate cleanup of collective conduits 60 once the particular surgical procedure has been concluded. Protection of collective conduits 60 is important since it significantly reduces cleanup time and thereby limits damage to collective conduits 60 which would otherwise result from collective conduits 60 being subjected to vigorous cleaning. Protective sheath 10 also reduces the likelihood of cross contamination resulting from inadequate cleanup and/or failure of the subsequent cold sterilization process of collective conduits 60.

Protective sheath 10 is removed from collective conduits 60 by releasing drawstring 11 and individually uncoupling connectors 34, 44, and 54 from their respective units and then pulling the respective conduit, monitor conduit 32, power conduit 42, and water conduit 52, through shield 14 and then the rest of the way through fabric sleeve 12. Protective sheath 10 is then discarded into an appropriate waste receptacle having served its purpose in shielding collective conduits from liquid contaminants.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A protective cover for surgical conduits comprising:
   a tubular element fabricated from a fabric-like material and having a first diameter and a first length, said first diameter being larger than a second diameter, said second diameter representing a diameter of the surgical conduits, said first length being shorter than a second length, said second length representing a length of the surgical conduits, said tubular element including a first end and a second end, said first end comprising a shield mounted to said first end, said shield comprising a planar element having a hole therethrough, said hole having a diameter corresponding to said first diameter of said tubular element, said shield including a guide member adjacent said hole and extending into said tubular element, said guide member forming a basal element, said shield being mounted to said first end with said tubular element being coupled to said hole, said hole providing access to the interior of said tubular element, said tubular element being foldable upon said basal element, said guide member having an open end to accommodate inserting the surgical conduits through said shield and said guide member into said tubular element, said guide member comprising opposing channel members, said opposing channel members being separable to accommodate passage of instruments heads affixed to the surgical conduits.

2. The protective cover defined in claim 1 wherein said tubular element comprises retainer means for selectively holding said tubular element in a foreshortened configuration on said opposing channel members.

3. A protective cover for removably constricting a plurality of surgical conduits as a bundle comprising:
   a tubular element fabricated from a liquid resistant fabric and having a length shorter than the plurality of surgical conduits and a cross sectional area larger than a cross sectional area of an aggregate of the plurality of surgical conduits, said tubular element including a first end and a second end;
   handle means for pulling said tubular element over the plurality of surgical conduits, said handle means comprising a shield having a hole therethrough, said hole having a cross sectional area corresponding to said cross sectional area of said tubular element, said shield being mounted to said first end of said tubular element at said hole;

a guide member adjacent said hole in said shield, said guide member comprising opposing channel members, said opposing channel members being separable to accommodate passage of instrument heads affixed to the surgical conduits; and a drawstring secured at said second end of said tubular element for cinching said second end of said tubular element against the plurality of surgical conduits.

4. A protective cover for a plurality of surgical conduits comprising:

a tubular element fabricated from a fabric-like material and having a first diameter and a first length, said first diameter being larger than a second diameter, said second diameter representing a diameter of an aggregate of the plurality of surgical conduits, said first length being shorter than a second length, said second length representing the length of the plurality of surgical conduits;

a handle means for pulling said tubular element over the plurality of surgical conduits, said handle means comprising a planar shield mounted to a first end of said tubular element, said shield comprising a diametrally enlarged planar element having a hole therethrough, said hole having a cross sectional area corresponding to said first diameter of said tubular element, said shield being mounted transversely to said first end with said tubular element being coupled to said hole, said hole providing access to an interior of said tubular element; and a guide member adjacent said hole in said shield, said guide member comprising opposing channel members, said opposing channel members holding said tubular element open to accommodate passage of the plurality of surgical conduits into said tubular element.

5. A restraining apparatus and protective cover for a plurality of surgical conduits comprising:

a tubular element fabricated from a liquid resistant fabric and having a length shorter than the plurality of surgical conduits and a cross sectional area larger than an aggregate cross sectional area of the combined plurality of surgical conduits, said tubular element including a first end and a second end;

a shield having a hole therethrough, said hole comprising an oval-shaped hole, said hole having an area corresponding to paid cross sectional area of said tubular element, said shield being mounted to said first end of said tubular element at said hole;

a guide member adjacent said hole, said guide member being mounted to said shield at said hole and extending interiorly into said tubular element, said guide member comprising opposing channel members, said opposing channel members being separable to accommodate passage of the plurality of surgical conduits, said guide member forming a basal element over which said tubular element is telescopically folded, said guide member holding said tubular element open to accommodate inserting the plurality of surgical conduits; and a drawstring mounted about said second end of said tubular element for cinching said second end of said tubular element against the plurality surgical conduits.

6. The restraining apparatus and protective cover defined in claim 5 wherein said shield includes retainer means for releasably holding said tubular element against said shield in a telescopically folded configuration.

7. A method for protecting and restraining a plurality of surgical conduits as a compact bundle comprising the steps of:

forming a tubular element from a liquid-resistant fabric;

preparing a shield as a planar element having a hole therethrough;

attaching said shield transversely to a first end of said tubular element with said hole forming an entry into said tubular element;

mounting a guide member adjacent said shield, said guide member having opposing channel members, said opposing channel members being separable thereby accommodating the plurality of surgical conduits passing into said tubular element;

slipping said tubular element over the plurality of surgical conduits by pulling on said shield and parting said channel members with the plurality of surgical conduits, said tubular element protecting the plurality of surgical conduits from liquid-based contaminants; and clipping said tubular element to a surgical drape thereby restraining the plurality of surgical conduits.

8. A method for protecting surgical conduits comprising the steps of:

forming a tubular element from a liquid-resistant fabric;

preparing a shield with a hole in said shield and attaching said shield to a first end of said tubular element with said hole forming an entry into said tubular element;

mounting a guide member to said shield, said guide member comprising a pair of opposing channel members hingedly affixed to said shield at said hole;

telescopically folding said tubular member over said guide member;

opening said opposing channel members while directing the surgical conduits through said tubular element by slipping said tubular element over the surgical conduits; and extending said tubular element by pulling said tubular element over the surgical conduits with said shield and thereby enclosing at least a portion of the surgical conduits and thereby protecting the surgical conduits.

9. The method defined in claim 8 wherein said preparing step includes mounting a drawstring to a second end of said tubular element for cinching said second end of said tubular element to the surgical conduits and holding said second end while pulling said shield and said first end along the surgical conduits.

10. The method defined in claim 8 wherein said preparing step includes mounting a retainer means on said shield for releasably holding said tubular element against said shield in a telescopically folded configuration.

* * * * *